(12) United States Patent
Palsdottir et al.

(10) Patent No.: US 11,266,926 B2
(45) Date of Patent: Mar. 8, 2022

(54) FLUORINATED CROWN ETHERS AND METHODS AND SYSTEMS FOR EXTRACTION OF LITHIUM USING SAME

(71) Applicant: Cornell University, Ithaca, NY (US)

(72) Inventors: Arna Palsdottir, Ithaca, NY (US); Jefferson W. Tester, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 16/643,284

(22) PCT Filed: Aug. 30, 2018

(86) PCT No.: PCT/US2018/048911
§ 371 (c)(1),
(2) Date: Feb. 28, 2020

(87) PCT Pub. No.: WO2019/046616
PCT Pub. Date: Mar. 7, 2019

(65) Prior Publication Data
US 2020/0346137 A1 Nov. 5, 2020

Related U.S. Application Data

(60) Provisional application No. 62/551,858, filed on Aug. 30, 2017.

(51) Int. Cl.
*B01D 11/04* (2006.01)
*C02F 1/26* (2006.01)
(Continued)

(52) U.S. Cl.
CPC ...... *B01D 11/0492* (2013.01); *B01D 11/0203* (2013.01); *B01D 11/0288* (2013.01);
(Continued)

(58) Field of Classification Search
CPC ............ B01D 11/0492; B01D 11/0407; B01D 11/0488; B01D 11/0403; B01D 11/0203;
(Continued)

(56) References Cited

U.S. PATENT DOCUMENTS

| 4,519,996 A | 5/1985 | Knochel et al. |
| 5,132,436 A | 7/1992 | Engebrecht et al. |

(Continued)

FOREIGN PATENT DOCUMENTS

| CN | 103785358 A | 5/2014 |
| JP | S6256485 A | 3/1987 |
| JP | S6272683 A | 4/1987 |

OTHER PUBLICATIONS

Chun-Ze Lai et al, "Cation-Coordinating Properties of Perfluoro-15-Crown-5", Journal of Fluoro Chemistry, Published 2010, vol. 131 (1), published Sep. 19, 2009 (Year: 2009).*
(Continued)

*Primary Examiner* — Joseph W Drodge
(74) *Attorney, Agent, or Firm* — Johnson, Marcou, Issacs & Nix, LLC; Paul J. Roman, Jr.

(57) ABSTRACT

The present disclosure provides fluorinated crown ethers. The fluorinated crown ethers have one or more pendant fluorinated groups (e.g., thioether groups with a terminal fluorinated group). The fluorinated crown ethers have desirable solubility in supercritical carbon dioxide. Also provided are methods and systems for removal of lithium (e.g., lithium ions) from aqueous samples using the fluorinated crown ethers coupled with lipophilic cation exchangers.

18 Claims, 6 Drawing Sheets

(51) Int. Cl.

| | | |
|---|---|---|
| *C07D 323/00* | (2006.01) | |
| *C22B 26/12* | (2006.01) | |
| *C22B 3/30* | (2006.01) | |
| *B01J 20/26* | (2006.01) | |
| *C02F 1/42* | (2006.01) | |
| *B01D 11/02* | (2006.01) | |
| *B01J 39/08* | (2017.01) | |
| *G01N 1/42* | (2006.01) | |
| *C22B 3/26* | (2006.01) | |
| *G01N 1/40* | (2006.01) | |
| *C02F 101/10* | (2006.01) | |
| *C02F 103/08* | (2006.01) | |
| *C02F 103/10* | (2006.01) | |

(52) U.S. Cl.
CPC ...... *B01D 11/0407* (2013.01); *B01D 11/0488* (2013.01); *B01J 20/26* (2013.01); *B01J 39/08* (2013.01); *C02F 1/26* (2013.01); *C02F 1/42* (2013.01); *C07D 323/00* (2013.01); *C22B 3/304* (2021.05); *C22B 26/12* (2013.01); *G01N 1/40* (2013.01); *C02F 2001/425* (2013.01); *C02F 2101/10* (2013.01); *C02F 2103/08* (2013.01); *C02F 2103/10* (2013.01)

(58) Field of Classification Search
CPC .. B01D 11/028; B01D 11/0288; B01D 61/10; B01D 2311/2623; C22B 3/304; C22B 26/12; C02F 1/26; C02F 2101/10; C02F 2103/08; C02F 2103/10; C02F 1/42; C02F 2001/425; C07D 323/00; Y02P 20/54; Y02P 10/20; B01J 20/20; B01J 20/26; B01J 20/262; B01J 39/08; B01J 39/16; B01J 39/18; B01J 39/19; B01J 39/26; G01N 1/10; G01N 1/40; G01N 1/405; G01N 2001/4061; G01N 33/18; G01N 33/1813

See application file for complete search history.

(56) References Cited

U.S. PATENT DOCUMENTS

| | | | |
|---|---|---|---|
| 5,245,021 A | | 9/1993 | Engebrecht et al. |
| 5,356,538 A | | 10/1994 | Wai et al. |
| 5,698,169 A | * | 12/1997 | Hawthorne ............. G21F 9/007 |
| | | | 423/2 |
| 5,865,994 A | | 2/1999 | Riviello et al. |
| 6,176,895 B1 | | 1/2001 | DeSimone et al. |
| 6,322,702 B1 | * | 11/2001 | Moyer ................... C22B 3/262 |
| | | | 210/634 |
| 7,105,095 B2 | | 9/2006 | Yaho et al. |
| 2002/0115566 A1 | | 8/2002 | Sessler et al. |
| 2012/0012529 A1 | * | 1/2012 | De Souza .......... B01D 11/0492 |
| | | | 210/663 |
| 2015/0143954 A1 | * | 5/2015 | Neumann ............... C22B 59/00 |
| | | | 75/401 |

OTHER PUBLICATIONS

Lee, et al., Effect of Structural Variation within Lipophilic N-(X)sulfonyl Carbamoyl Lariat Ethers on the Selectivity and Efficiency of Competitive Alkali Metal Cation Extraction into Chloroform, Analytical Chemistry, May 1, 2002, vol. 74, No. 9, pp. 2177-2183.

Pubchem, Substance Record for SID 78487766, Jun. 12, 2009, 5 pages. https://pubchem.ncbi.nim.nih.gov/substance/78487766.

Hou, H., et al., DFT study of a series of crown-4 ethers and their selectivity trend for alkali metal cations: Li+ and Na+, Journal of Molecular Modeling, Nov. 13, 2008, vol. 15, pp. 105-111.

Bartsch, R.A., et al., High Lithium Selectivity in Competitive Alkali-Metal Solvent Extraction by Lipophilic Ccrown Carboxylic Acids, J. Am. Chem. Soc., Aug. 1, 1985, vol. 107, No. 17, pp. 4997-4998.

Kataky, R., et al., Comparative Performance of 14-Crown-4 Derivatives as Lithium-selective Slectrodes, Analyst, Feb. 1991, vol. 116, No. 2, pp. 135-140.

Bartsch, R.A., et al., Influence of ring substituents and matrix on lithium / sodium selectivity of 14-crown-4 and benzo-13-crown-4-compounds, Analytica Chimica Acta, Feb. 12, 1993, vol. 272, No. 2, pp. 285-292.

Torrejos, R.E.C., et al., (3971) Lithium Selective 14-Crown-4 Ethers: Synthesis, Polymerization and its Application for the Recovery of Lithium from Dilute Solutions, AIChE annual Meeting, Oct. 31, 2017, 3 pages.

Wakita, R., et al., C-pivot lariat ethers bearing an electron-donating side arm as lithium cation selective extractants, J. Org. Chem, Apr. 1, 1990, vol. 55, No. 9, pp. 2752-2756.

Kim, H., et al., Decontamination of Heavy Metal in Soil by Using Supercritical Carbon Dioxide, Transactions of the Krean Nuclear Society Sprint Meeting, May 29, 2014, 3 pages.

Elshani, S., et al., Lariat Ether Carboxylic Acids, O-Benzylhydroxamates and Hydroxamic Acids with Fluorinated Substituents: Synthesis, Metal Ion Complexation and Solubility in Supercritical Carbon Dioxide, Tetrahedron, Jun. 30, 2000, vol. 56, No. 27, pp. 4651-4657.

* cited by examiner

FLUORINATED CROWN ETHERS AND METHODS AND SYSTEMS FOR EXTRACTION OF LITHIUM USING SAME

CROSS REFERENCE TO RELATED APPLICATIONS

This application claims priority to U.S. Provisional Application No. 62/551,858, filed on Aug. 30, 2017, the disclosure of which is hereby incorporated by reference.

FIELD OF THE DISCLOSURE

The disclosure generally relates to fluorinated crown ethers. More particularly the disclosure relates to lithium extraction methods using fluorinated crown ethers.

BACKGROUND OF THE DISCLOSURE

Selective lithium extraction from aqueous solutions containing dissolved lithium salts is generally performed using size selective 14-crown-4 ethers. The 14-crown-4 ethers synthesized to date have enabled efficient lithium extraction into traditional organic solvents such as chloroform and methylene chloride. With an increased focus on the use of environmentally friendly solvents in industry, supercritical carbon dioxide has emerged as an alternative and environmentally friendly solvent for extractions, reactions and catalysis. The 14-crown-4 ethers synthesized and utilized for lithium extraction to date are not soluble enough in supercritical carbon dioxide to enable the operation of efficient and economically viable extraction processes of lithium with supercritical carbon dioxide as a solvent. Researchers have attempted to solve a similar problem, the extraction of a range of other alkali metals than lithium into supercritical carbon dioxide, by pairing selective crown ether extractants with highly soluble cation exchangers. While this enables the selective extraction of cesium, potassium, and sodium ions into supercritical carbon dioxide it does not enable the operation of a continuous extraction process since the crown ether does not solubilize in the supercritical carbon dioxide until a complex is formed with the alkali metal and the cation exchanger. The need to operate in batch mode is highly detrimental to the efficiency and economics of the extraction process. Additionally, this type of process has never been operated for lithium extraction, only for the extraction of sodium, potassium and cesium. To enable continuous lithium extraction a new type of 14-crown-4 ether extractant is necessary, one that is soluble in supercritical carbon dioxide.

The extraction systems developed to date suffer from low extractant solubility for lithium extractants in supercritical carbon dioxide which inhibits the operation of continuous extraction processes. Researchers have developed systems that could enable continuous operations for lithium extraction into traditional organic solvents and systems for batch extraction of sodium, potassium and cesium using supercritical carbon dioxide but until now, suitable lithium extractants have not been available to develop a continuous lithium extraction process that is operated using supercritical carbon dioxide.

Based on the foregoing, there exists and ongoing an unmet need for improved crown ethers for extraction methods.

SUMMARY OF THE DISCLOSURE

The present disclosure provides fluorinated crown ethers and methods of making same. The present disclosure also provides methods of using fluorinated crown ethers.

In an aspect, the present disclosure provides fluorinated crown ethers. The fluorinated crown ethers have an exocyclic fluorinated thioether group with a terminal fluorinated group. The fluorinated crown ethers can be referred to as fluoroponytailed 14-crown-4 ethers. The fluorinated crown ethers comprise a 14-member ring with 4 oxygen atoms. The fluorinated crown ethers can be referred to as fluorinated 14-crown-4 ethers. The fluorinated crown ethers comprise one or more fluorinated groups that are pendant from the 14-member ring. In the case where the fluorinated crown ether has two or more fluorinated groups, the fluorinated groups may be the same or different fluorinated groups. It is desirable that the one or more fluorinated groups are spatially separated from the 14-member ring. In various examples, the one or more fluorinated groups are spatially separated from the 14-member ring. These groups can be referred to as exocyclic fluorinated groups or fluoroponytail groups. In an example, a fluorinated crown ether comprise multiple exocyclic fluorinated groups (e.g., 2, 3, 4, 5, 6, 7, 8, 9, or 10 exocyclic fluorinated groups). The fluorinated group(s) is/are pendant from a methylene group of the crown ether ring (e.g., covalently bonded to a carbon of the crown ether ring). The fluorinated crown ethers have a desirable solubility in supercritical carbon dioxide.

Examples of exocyclic fluorinated groups include groups with terminal fluorinated groups. In various examples, exocyclic fluorinated groups are thioether groups that have a terminal fluorinated group. The terminal fluorinated group comprises one or more fluorine substituents. The terminal fluorinated group can be a perfluorinated group or partially fluorinated group. Examples of terminal groups include, but are not limited to, fluorinated alkyl groups and fluorinated aryl groups.

In an aspect, the present disclosure provides uses of fluorinated crown ethers of the present disclosure. The fluorinated crown ethers can be used in conjunction with a cation exchanger to selectively remove (e.g., selectively remove) lithium (e.g., lithium ions) from aqueous solutions.

In various examples, the fluorinated crown ethers of the present disclosure are used in conjunction with a cation exchanger for selective extraction of lithium (e.g., using supercritical carbon dioxide) from a range of lithium (e.g., lithium salts such as, for example, lithium chloride, lithium sulfate, and the like, and combinations thereof) containing aqueous solutions, such as, for example, brines (e.g., traditional lithium brines, oilfield brines, and the like), geothermal waters, produced fluids in fracking operations, wastewater from a range of industries, desalination plant runoff, battery recycling fluids and seawater.

In various examples, a method for removing (e.g., selectively removing) lithium ions from an aqueous sample comprising lithium ions comprises: contacting the aqueous sample comprising lithium ions with one or more fluorinated crown ethers of the present disclosure, along with a cation exchanger, and separating the aqueous sample that has been contacted with the one or more fluorinated crown ether and cation exchanger resulting in removal of at least a portion of or all of the lithium ions from the aqueous sample.

In an aspect, the present disclosure provides systems for removal (e.g., selective removal) of lithium ions from aqueous solutions. In various examples, the present disclosure describes a supercritical carbon dioxide soluble 14-crown-4 ether extractant and paired it with a lipophilic cation exchanger, enabling the development of a supercritical fluid extraction process of lithium ions from aqueous solutions. The process is operable in a continuous fashion by using the pairing of the novel carbon dioxide soluble 14-crown-4 ether extractant and the cation exchanger. Omitting either chemical results in a very limited extraction of lithium ions. The systems can be configured to process various volumes of aqueous samples. The systems can be lab scale systems or industrial scale systems.

BRIEF DESCRIPTION OF THE FIGURES

For a fuller understanding of the nature and objects of the disclosure, reference should be made to the following detailed description taken in conjunction with the accompanying figures.

DETAILED DESCRIPTION OF THE DISCLOSURE

Although claimed subject matter will be described in terms of certain embodiments and examples, other embodiments and examples, including embodiments and examples that do not provide all of the benefits and features set forth herein, are also within the scope of this disclosure. Various structural, logical, and process step changes may be made without departing from the scope of the disclosure.

Ranges of values are disclosed herein. The ranges set out a lower limit value and an upper limit value. Unless otherwise stated, the ranges include all values to the magnitude of the smallest value (either lower limit value or upper limit value) and ranges between the values of the stated range.

The present disclosure provides fluorinated crown ethers and methods of making same. The present disclosure also provides methods of using fluorinated crown ethers.

In an aspect, the present disclosure provides fluorinated crown ethers. The fluorinated crown ethers may have an exocyclic fluorinated thioether group with a terminal fluorinated group. The fluorinated crown ethers can be referred to as fluoroponytailed 14-crown-4 ethers.

The fluorinated crown ethers comprise a 14-member ring with 4 oxygen atoms. The fluorinated crown ethers can be referred to as fluorinated 14-crown-4 ethers.

The fluorinated crown ethers comprise one or more fluorinated groups that are pendant from the 14-member ring. In the case where the fluorinated crown ether has two or more fluorinated groups, the fluorinated groups may be the same or different fluorinated groups. It is desirable that the one or more fluorinated groups are spatially separated from the 14-member ring. In various examples, the one or more fluorinated groups are spatially separated (e.g., via a non-fluorinated group) from the 14-member ring. These groups can be referred to as exocyclic fluorinated groups or fluoroponytail groups. In an example, a fluorinated crown ether comprise multiple exocyclic fluorinated groups (e.g., 2, 3, 4, 5, 6, 7, 8, 9, or 10 exocyclic fluorinated groups). The fluorinated group(s) is/are pendant from a methylene group of the crown ether ring (e.g., covalently bonded to a carbon of the crown ether ring).

Examples of exocyclic fluorinated groups include groups with terminal fluorinated groups. A terminal fluorinated group may be linked via a non-fluorinated group to a crown ether ring. In various examples, exocyclic fluorinated groups are thioether groups that have a terminal fluorinated group.

The terminal fluorinated group comprises one or more fluorine substituents. The terminal fluorinated group can be a perfluorinated group or partially fluorinated group. Examples of terminal groups include, but are not limited to, fluorinated alkyl groups and fluorinated aryl groups.

Examples of terminal groups include, but are not limited to, the following:

where n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F.

Additional examples of terminal groups include, but are not limited to, the following:

where m is, independently at each occurrence, 0, 1, 2, 3, 4, 5, 6, 7, 8, 9, 10, 11, 12, 13, 14, 15, 16, 17, 18, 19, or 20.

Examples of exocyclic fluorinated groups include, but are not limited to, the following:

where n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F.

Additional examples of exocyclic fluorinated groups include, but are not limited to:

where m is, independently at each occurrence, 0, 1, 2, 3, 4, 5, 6, 7, 8, 9, 10, 11, 12, 13, 14, 15, 16, 17, 18, 19, or 20.

Figure 1:
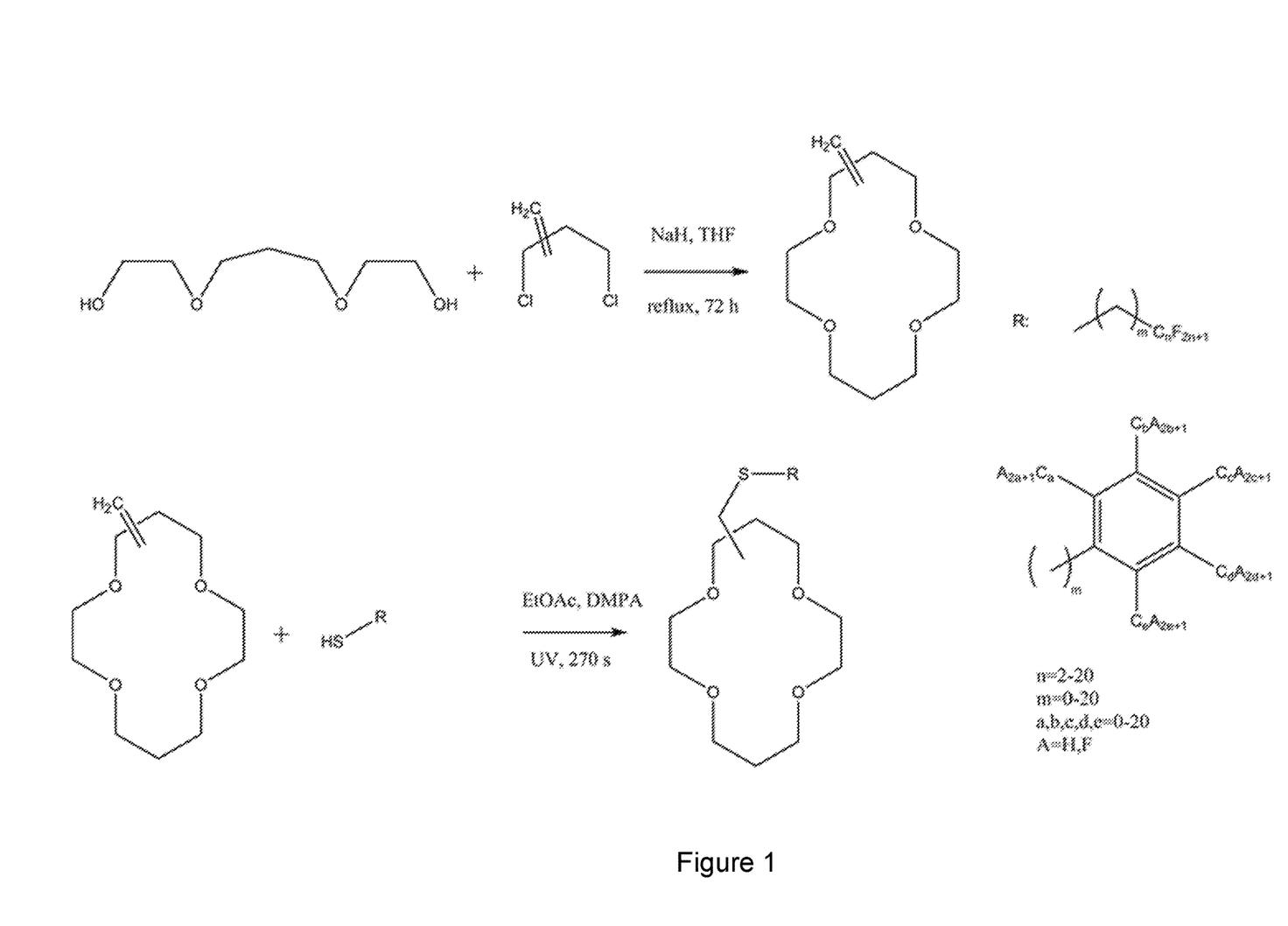
FIG. 1 shows a synthetic pathway for making a novel type of lithium selective 14-crown-4 ethers that are soluble in supercritical carbon dioxide.

In an example, a fluorinated crown ether has the following structure:

For example, this fluorinated crown ether is made using the synthetic pathway described in FIG. 1. Examples of characterization data for this fluorinated crown ether are shown in FIGS. 3-6.

Other non-limiting examples of fluorinated crown ethers include:

The fluorinated crown ethers have a desirable solubility in supercritical carbon dioxide. In various example, the fluorinated crown ethers have a solubility in supercritical carbon dioxide of 0.01 mol/L or greater, 0.02 mol/L or greater, 0.05 mol/L or greater, 0.1 mol/L or greater, 0.15 mol/L or greater, or 0.2 mol/L or greater. In various examples, the fluorinated crown ethers have a solubility in supercritical carbon dioxide of 0.02 to 0.26 mol/L, including all 0.01 mol/L values and ranges therebetween, for example, at temperatures from 40° C. to 100° C., including all integer ° C. values and ranges therebetween, and/or from 100 bar to 300 bar, including all integer bar values and ranges therebetween.

In various examples, the extraction of lithium (e.g., lithium ions) with a fluorinated crown ether and a cation exchanger has a selectivity of $K_{ex,Li}/K_{ex,Na}=2.25$ for lithium ions over sodium ions. For comparison, extraction of lithium ions with methylene-14-crown-4, a previously synthesized and non-fluorinated crown ether, and a cation exchanger has a selectivity of $$\frac{K_{ex,Li}}{K_{ex,Na}} = 1,$$

i.e. no selectivity. In an example, a fluorinated crown ether of the present disclosure exhibits in a selectivity for lithium ions over sodium ions of 1.5 or greater, 1.6 or greater, 1.7 or greater, 1.8 or greater, 1.9 or greater, 2 or greater, 2.1 or greater, 2.2 or greater, or 2.3 or greater.

In an aspect, the present disclosure provides uses of fluorinated crown ethers of the present disclosure. The fluorinated crown ethers can be used in conjunction with a cation exchanger to selectively remove (e.g., selectively remove) lithium from aqueous solutions. As used herein, the term "lithium" includes lithium species, such as, for example, lithium ions.

In various examples, the fluorinated crown ethers of the present disclosure are used in conjunction with a cation exchanger for selective extraction of lithium (e.g., using supercritical carbon dioxide) from a range of lithium (e.g., lithium salts such as, for example, lithium chloride, lithium sulfate, and the like, and combinations thereof) containing aqueous solutions, such as, for example, brines (e.g., traditional lithium brines, oilfield brines, and the like), geothermal waters, produced fluids in fracking operations, wastewater from a range of industries, desalination plant runoff, battery recycling fluids and seawater.

In various examples, a method for removing (e.g., selectively removing) lithium ions from an aqueous sample comprising lithium ions comprises: contacting the aqueous sample comprising lithium ions with one or more fluorinated crown ethers of the present disclosure, along with a cation exchanger, and separating the aqueous sample that has been contacted with the one or more fluorinated crown ether and cation exchanger resulting in removal of at least a portion of or all of the lithium ions from the aqueous sample.

Without intending to be bound by any particular theory, it is considered that the lithium ions bond (e.g., coordinate) to the fluorinated crown ethers and the cation exchanger to form a complex. The bonding is such that the lithium ions are removed from the aqueous sample when the crown ether and cation exchanger that have been contacted with sample are removed from the sample.

The lithium ions can, after separation from the fluorinated crown ethers, be isolated as metal salts. In various non-limiting examples, the metal salts are hydroxide salts, chloride salts, sulfate salts, phosphate salts, carbonate salts, or a combination thereof.

The process can have various lithium ion removal efficiency. In an example, at least a portion of the lithium ions are removed from the aqueous sample. In various examples, 20 to 100% by weight, including all 0.1% by weight values and ranges therebetween, of the lithium ions are removed from the aqueous sample. In various examples, at least 20%, at least 40%, at least 50%, at least 70%, at least 90%, at least 95%, at least 99%, at least 99.5%, at least 99.9%, or 100% of the lithium ions are removed from the aqueous sample. The amount of lithium ions in the aqueous sample can be determined by methods known in the art. In various examples, the amount of lithium ions in the aqueous sample is determined by inductively coupled plasma mass spectrometry (ICP-MS) or inductively coupled plasma atomic emission spectrometry (ICP-EAS/OES).

The process can selectively remove lithium ions. In an example, at least a portion of the lithium ions are removed from an aqueous sample comprising other metal ions. In various examples, lithium ions are removed from an aqueous sample comprising lithium and, optionally, other metal ions such as for example, sodium, potassium, calcium, magnesium, boron, or a combination thereof. In an example, a method of the present disclosure exhibits in a selectivity for lithium ions over sodium ions of 1.5 or greater, 1.6 or greater, 1.7 or greater, 1.8 or greater, 1.9 or greater, 2 or greater, 2.1 or greater, 2.2 or greater, or 2.3 or greater.

The contacting can be carried out in a mixture (e.g., a heterogeneous mixture). In addition to fluorinated crown ether(s), the mixture can also comprise carbon dioxide and/or one or more solvents/co-solvents and/or one or more cation exchangers, which can be supercritical carbon dioxide-soluble cation exchangers. Examples of solvents include, but are not limited to, carbon dioxide (e.g., supercritical carbon dioxide), alcohols (e.g., methanol, ethanol, and the like), chlorinated solvents (e.g., methylene chloride, chloroform, and the like). Examples of cation exchangers (e.g., supercritical carbon dioxide-soluble cation exchangers) include, but are not limited to, organic acids such as, for example, phosphoric acids, phosphinic acids, sulfonic acids, carboxylic acids, and the like, and combinations thereof. Non-limiting examples of phosphoric acids include dialkylphosphoric acids (e.g., HDEHP (di-(2-ethylhexyl)phosphoric acid) and the like) and the like. Non-limiting examples of phosphinic acids include bis(2,4,4-trimethylphentyl)phosphinic acid, perfluorinated phosphinic acids, and the like. Non-limiting examples of sulfonic acids include dialkylnapthalene sulfonic acids (e.g., HDDNS (di-dodecylnaphthalenesulfonic acid) and the like), perfluorinated sulfonic acids (e.g., PFOS (heptadecafluorooctanesulfonic acid) and the like), and the like), and the like. Non-limiting examples of carboxylic acids include perfluorinated carboxylic acids (e.g., PFOA (perfluorooctanoic acid), pentadecafluorooctanoic acid, and the like), and the like. In various examples, the contacting is carried out in a mixture comprising the aqueous sample, the one or more fluorinated crown ether, carbon dioxide (e.g., supercritical carbon dioxide), one or more cation exchanger, and, optionally, one or more co-solvent.

The contacting can be carried out with only carbon dioxide (e.g., supercritical carbon dioxide) as a solvent, without a co-solvent. In an example, the contacting is carried out in a mixture comprising, consisting of, or consisting essentially of the aqueous sample, the one or more fluorinated crown ether, carbon dioxide (e.g., supercritical carbon dioxide), and one or more cation exchanger.

The contacting can be carried out under various conditions. In various examples, temperatures ranging from 30° C. to 200° C., including all integer ° C. values and ranges therebetween, and/or pressures from 74 bar to 350 bar, including all integer bar values and ranges therebetween, and/or contacting time between the two phases ranges from seconds to hours (e.g., 1 second to 10 hours, including all integer second values and ranges therebetween).

An aqueous sample that has been contacted with the one or more fluorinated crown ether and cation exchanger dissolved in a solvent (e.g. supercritical carbon dioxide) can be separated from the one or more fluorinated crown ether and cation exchanger dissolved in a solvent (e.g. supercritical carbon dioxide) resulting in removal of at least a portion of or all of the lithium ions from the aqueous sample by methods known in the art. For example, the aqueous sample is separated from the one or more fluorinated crown ether and cation exchanger dissolved in a solvent in a gravitational settler or through other methods relying on the density difference between the aqueous sample and the solvent (e.g. supercritical carbon dioxide).

The lithium ions can be separated from the fluorinated crown ether and cation exchanger after separation from the aqueous sample. For example, the lithium ions are separated from the fluorinated crown ether and cation exchanger by washing with a mineral acid (e.g. hydrochloric acid, phosphoric acid, sulfuric acid, nitric acid, and the like, and combinations thereof). The metal ions can be further processed by precipitation, electrolysis or other methods, for example, to make lithium salts (e.g. lithium carbonate, lithium phosphate, and the like) or a lithium hydroxide solution.

The fluorinated ethers can be recycled (e.g., reused in another/subsequent contacting step). A method can further comprise removal of the metal ions (e.g., lithium ions) from the crown ether and the cation exchanger and the crown ether can be contacted with the sample again or contacted with another sample.

A method can be run in various modes. In an example, a method is run in continuous mode. In an example, a method is run in semi-batch mode. In another example, a method is run in batch mode.

The steps of the method described in the various embodiments and examples disclosed herein are sufficient to carry out the methods of the present disclosure. Thus, in an example, a method consists essentially of a combination of steps of the methods disclosed herein. In another example, a method consists of such steps.

In an aspect, the present disclosure provides systems for removal (e.g., selective removal) of lithium ions from aqueous solutions. Examples of systems are provided herein.

In various examples, the present disclosure describes a supercritical carbon dioxide soluble 14-crown-4 ether extractant and paired it with a lipophilic cation exchanger, enabling the development of a supercritical fluid extraction process of lithium ions from aqueous solutions. The process is operable in a continuous fashion by using the pairing of the novel carbon dioxide soluble 14-crown-4 ether extractant and the cation exchanger. Omitting either chemical results in a very limited extraction of lithium ions.

The systems can be configured to process various volumes of aqueous samples. The systems can be lab scale systems or industrial scale systems. In various examples, a system is configured to process volumes of aqueous samples ranging from 0.05 to 10 L or 10,000 to 100,000 L. In various examples, a system is configured to process volumes of aqueous samples ranging from 0.05 to 100,000 L.

Figure 2:
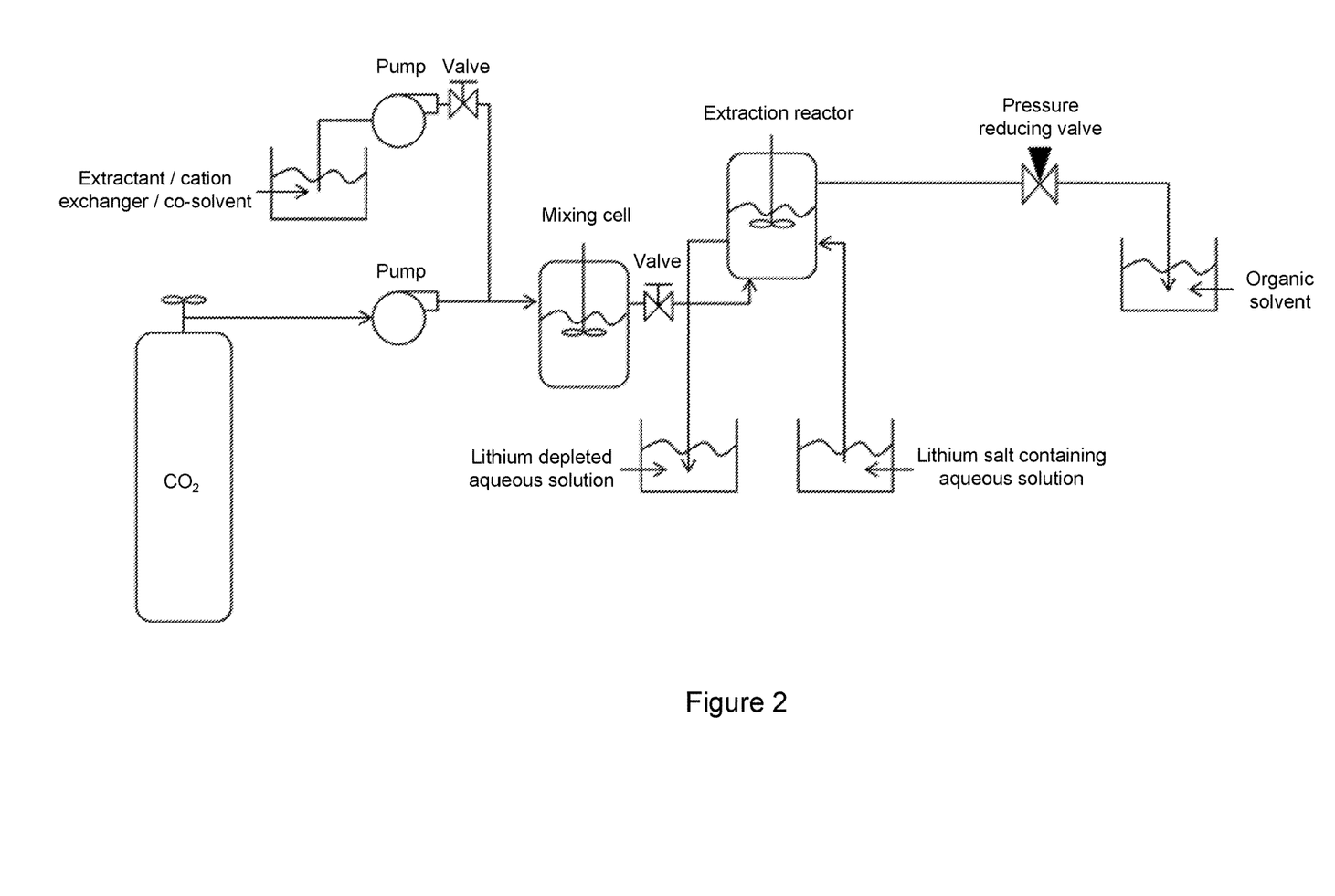
FIG. 2 shows an example of a system for lithium extraction.

FIG. 2 shows an example of a system for lithium extraction from an aqueous sample. The system in FIG. 2 includes a fluorinated crown ether extractant and cation exchanger source, which also may include a co-solvent. The system in FIG. 2 also includes a carbon dioxide source. Both of these sources are in fluid communication with a mixing cell, such as via valves and/or a pump. The mixing cell is in fluid communication with an extraction reactor, such as via a valve. The extraction reactor is in fluid communication with an aqueous solution source that provides a lithium ion containing aqueous solution. Lithium ions are extracted from the lithium ion containing aqueous solution in the extraction reactor into the supercritical carbon dioxide phase.

A pressure reducing valve is in fluid communication with the extraction reactor. A collection vessel is in fluid communication with the pressure reducing valve. The collection vessel collects condensed lithium containing complex.

The lithium ion containing aqueous solution can provide a lithium salt. Lithium depleted aqueous solution may be removed from the extraction reactor and sent to a tank.

The mixing cell in the system of FIG. 2 can operate at supercritical conditions. The system of FIG. 2 operates continuously or in a semi-batch mode.

Figure 3:
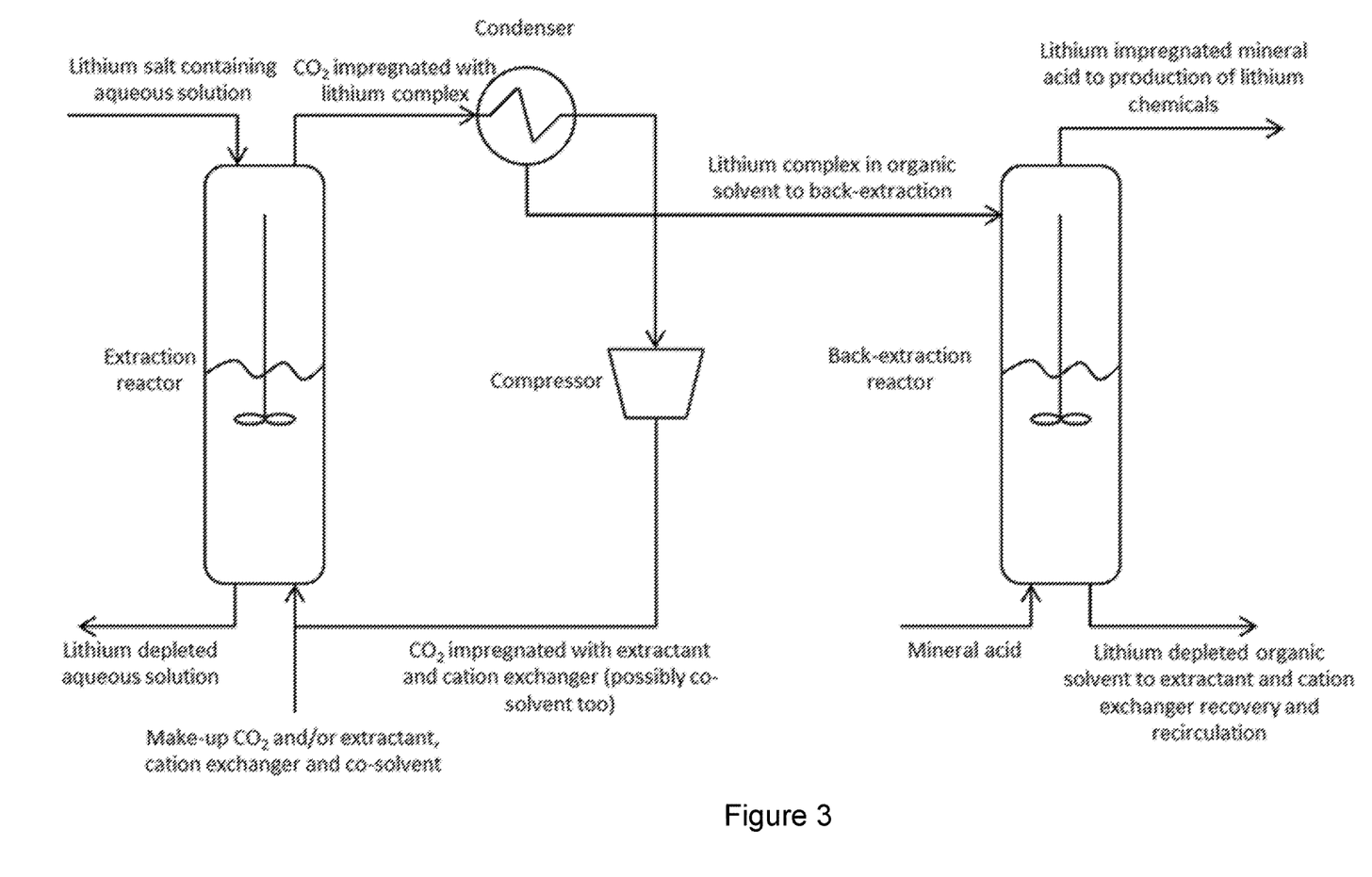
FIG. 3 shows an example of a system for lithium extraction.
Figure 4:
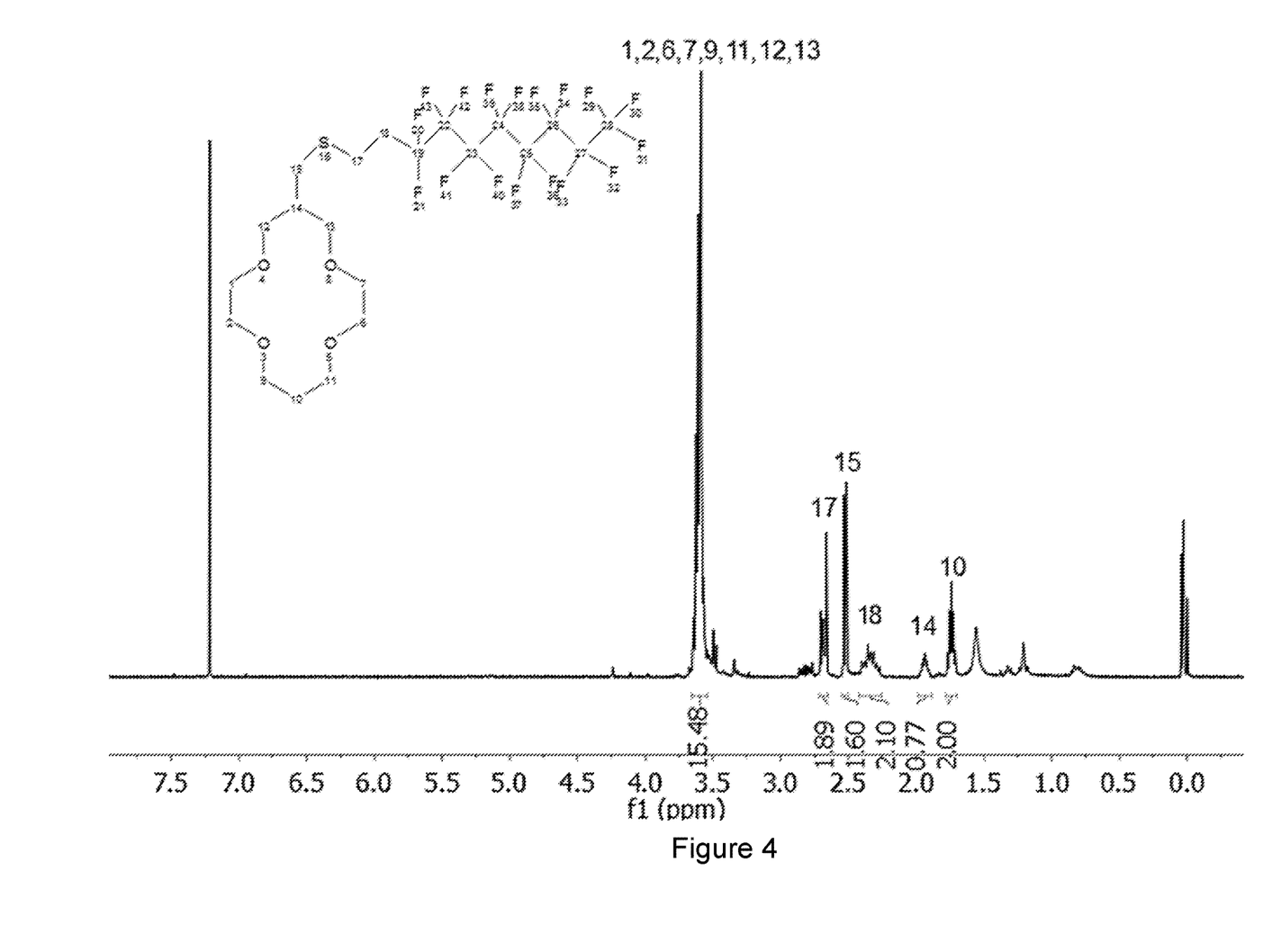
FIG. 4 shows a $^1$H NMR spectrum of a fluorinated 14-crown-4 compound.
Figure 5:
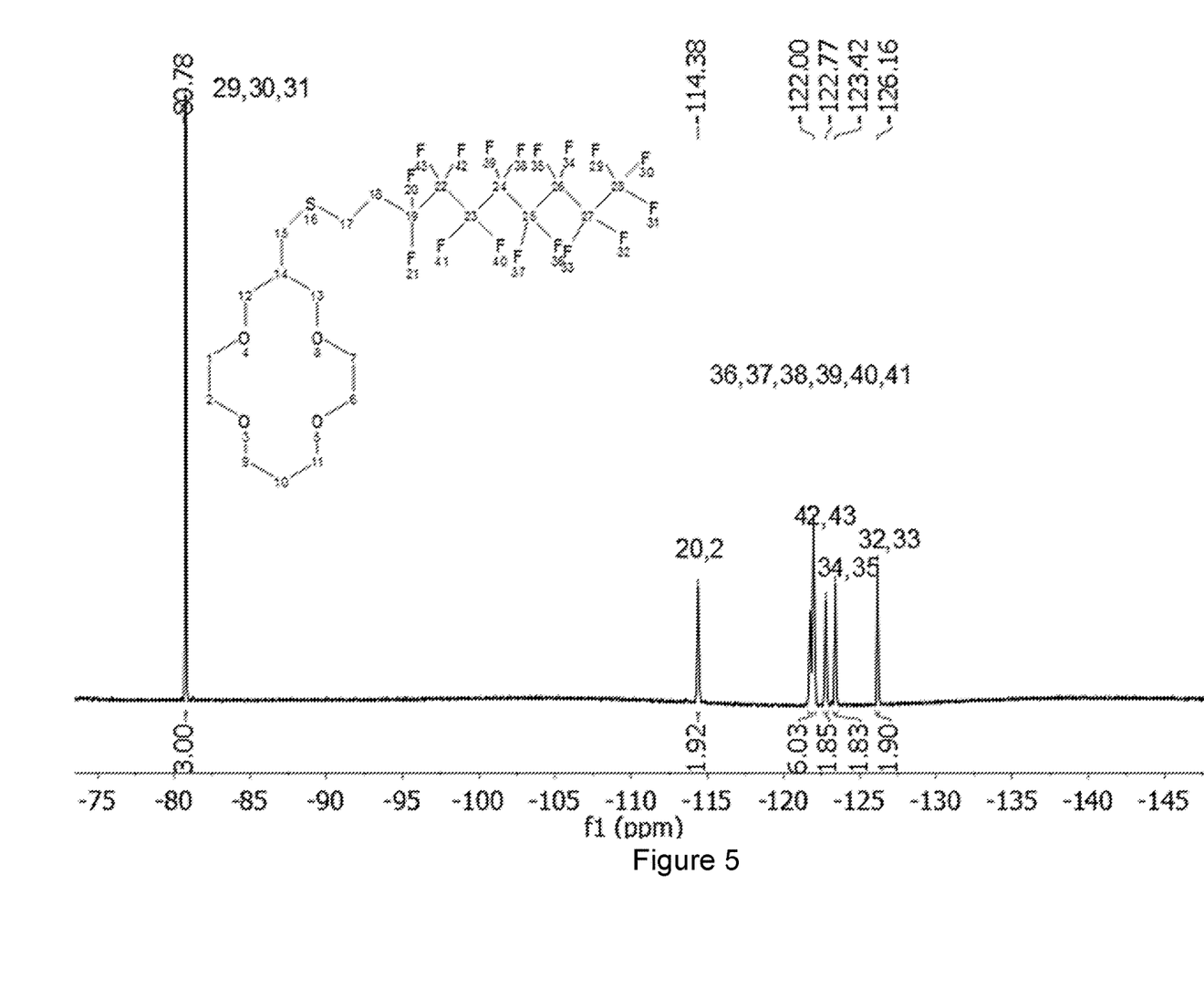
FIG. 5 shows a $^{19}$F NMR spectrum of a fluorinated 14-crown-4 compound.
Figure 6:
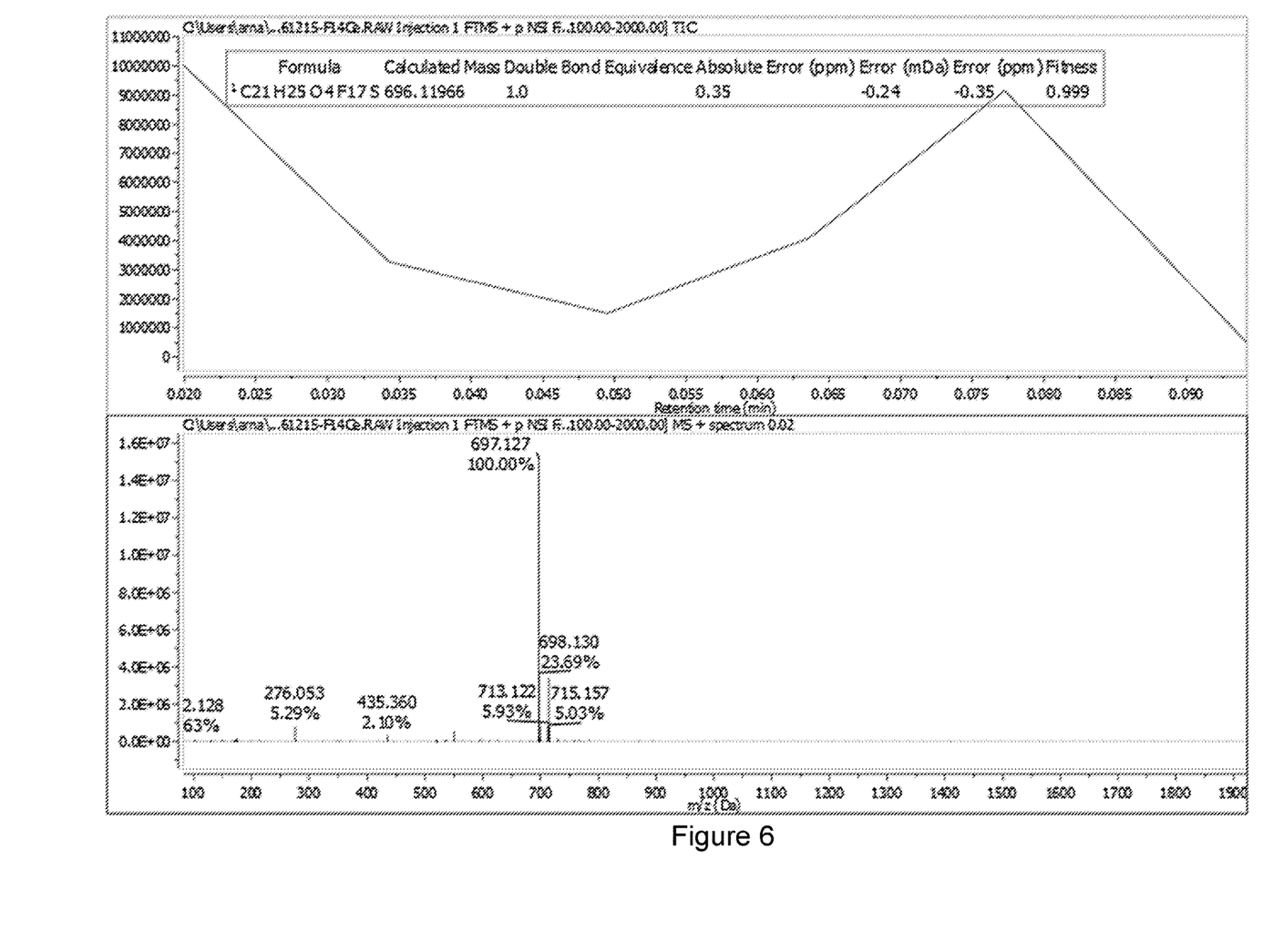
FIG. 6 shows a Direct Analysis in Real Time-High Resolution Mass Spectrometry (DART-HRMS) spectrum of a fluorinated 14-crown-4 compound.

FIG. 3 shows an example of a system for lithium extraction from an aqueous sample. The system in FIG. 3 includes an aqueous solution source that provides a lithium containing aqueous solution. This aqueous solution may include a lithium salt. The system in FIG. 3 also includes a carbon dioxide source. An extraction reactor is in fluid communication with the aqueous solution source and the carbon dioxide source. A condenser is in fluid communication with the extraction reactor. The condenser condenses at least some lithium containing complex from a carbon dioxide stream that includes the lithium containing complex into an organic solvent.

A compressor is in fluid communication with the condenser. The compressor compresses at least some of the carbon dioxide stream that is depleted of the lithium containing complex. The compressor may be in fluid communication with the extraction reactor, such that carbon dioxide impregnated with fluorinated crown ether extractant and cation exchanger (optionally with co-solvent) can be returned to the extraction reactor.

An extraction reactor (e.g., a second extraction reactor) is in fluid communication with the condenser. The organic solvent that includes the lithium containing complex is delivered to the second extraction reactor. A mineral acid source, first collection vessel, and second collection vessel are in fluid communication with the second extraction reactor. The first collection vessel collects lithium impregnated mineral acid. The contents of this collection vessel can be used in, for example, production of lithium chemicals. The second collection vessel collects lithium depleted organic solvent. The contents of the second collection vessel can be used in, for example, recovery of fluorinated crown ether extractant and cation exchanger and/or for recirculation.

A fluorinated crown ether extractant and cation exchanger source may be in fluid communication with the extraction reactor. Co-solvent may be provided with the fluorinated crown ether extractant and cation exchanger. The fluorinated crown ether extractant and cation exchanger and the carbon dioxide may both be delivered to the extraction reactor through one or more conduits. In an instance, fluorinated crown ether extractant and cation exchanger and the carbon dioxide may both be delivered to the extraction reactor through a shared conduit.

Carbon dioxide from the carbon dioxide source may be at a pressure at or above its critical point and/or is at a temperature at or above its critical point.

The system in FIG. 3 can operate continuously or in a semi-batch mode.

The following Statements provide examples of fluorinated crown ethers and methods of using same of the present disclosure:

Statement 1. A fluorinated crown ether having the following structure:

where R is a exocyclic fluorinated group and s is the number of exocyclic fluorinated groups and is 1, 2, 3, 4, 5, 6, 7, 8, 9, or 10.

Statement 2. A fluorinated crown ether according to Statement 1, where the exocyclic fluorinated group comprises a terminal fluorinated group.

Statement 3. A fluorinated crown ether according to Statement 1, where the terminal fluorinated group is selected from the group consisting of:

where n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F.

Statement 4. A fluorinated crown ether according to Statement 1, where R is selected from the group consisting of:

where n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F.

Statement 5. A method for removing (e.g., selectively removing) lithium (e.g., lithium ions) from an aqueous sample comprising lithium (e.g., lithium ions) comprising: contacting the aqueous sample comprising lithium ions with one or more fluorinated crown ether of the present disclosure (e.g., a fluorinated crown ether according to Statement 1) and a cation exchanger, separating the aqueous sample that has been contacted with the one or more fluorinated crown ether and cation exchanger resulting in removal of at least a portion of or all of the lithium ions from the aqueous sample. The fluorinated crown ether may exhibit a solubility and/or selectivity described herein.

Statement 6. A method according to Statement 5, further comprising removing lithium (e.g., lithium ions) from the one or more fluorinated crown ether and cation exchanger that has been contacted with the aqueous sample by washing the one or more fluorinated crown ether and cation exchanger that has been contacted with the sample with an acid as described herein (e.g., a mineral acid, such as, for example, a mineral acid solution).

Statement 7. A method according to Statement 6, where the one or more fluorinated crown ether is recycled (e.g., used in a subsequent contacting).

Statement 8. A method according to Statement 6, where the cation exchanger is contacted with the aqueous sample after the aqueous sample is contacted with the one or more fluorinated crown ether.

Statement 9. A method according to any one of Statements 5-8, where the contacting is carried out in a batch mode, semi-batch mode or a continuous mode.

Statement 10. A method according to any one of Statements 5-9, where the aqueous sample is selected from the group consisting of lithium brines, geothermal waters, oilfield brines, fluids produced in fracking operations, wastewater (e.g., industrial wastewater), desalination plant runoff, battery recycling fluids, and seawater.

Statement 11. A method according to any one of Statements 5-10, where the contacting is carried out in a mixture comprising the aqueous sample, one or more fluorinated crown ether, a cation exchanger, and carbon dioxide (e.g., supercritical or sub-critical carbon dioxide).

Statement 12. A system for removing (e.g., selectively removing) lithium ions from an aqueous sample comprising lithium (e.g., lithium ions) comprising: a fluorinated crown ether extractant and cation exchanger source; a carbon dioxide source; a mixing cell in fluid communication with the fluorinated crown ether and cation exchanger source and the carbon dioxide source; an aqueous solution source configured to provide a lithium ion containing aqueous solution; an extraction reactor in fluid communication with the mixing cell and the aqueous solution source, where lithium ions are extracted from the lithium ion containing aqueous solution in the extraction reactor into the supercritical carbon dioxide phase; a pressure reducing valve in fluid communication with the extraction reactor; and a collection vessel in fluid communication with the pressure reducing valve, where the collection vessel collects a condensed lithium containing complex.

Statement 13. A system according to Statement 12, where the mixing cell operates at supercritical conditions.

Statement 14. A system according to Statement 12, where the system operates continuously or in a semi-batch mode.

Statement 15. A system for removing (e.g., selectively removing) lithium ions from an aqueous sample comprising lithium (e.g., lithium ions) comprising: an aqueous solution source configured to provide a lithium containing aqueous solution; a carbon dioxide source; an extraction reactor in fluid communication with the aqueous solution source and the carbon dioxide source; a condenser in fluid communication with the extraction reactor, where the condenser condenses at least some lithium containing complex from a carbon dioxide stream that includes the lithium containing complex into an organic solvent; a compressor in fluid communication with the condenser, where the compressor compresses at least some of the carbon dioxide stream that is depleted of the lithium containing complex; a second extraction reactor in fluid communication with the condenser, where the organic solvent comprising the lithium containing complex is delivered to the second extraction reactor; a mineral acid source in fluid communication with the second extraction reactor; a first collection vessel in fluid communication with the second extraction reactor, where the first collection vessel collects lithium impregnated mineral acid; and a second collection vessel in fluid communication with the second extraction reactor, where the second collection vessel collects lithium depleted organic solvent.

Statement 16. A system according to Statement 15, further comprising a fluorinated crown ether extractant and cation exchanger source in fluid communication with the extraction reactor.

Statement 17. A system according to Statement 16, where the fluorinated crown ether extractant and cation exchanger source and the carbon dioxide source are both delivered to the extraction reactor through a conduit.

Statement 18. A system according to Statement 15-17, where carbon dioxide from the carbon dioxide source is at a pressure at or above its critical point and/or is at a temperature at or above its critical point.

Statement 19. A system according to Statement 15-18, where the compressor is in fluid communication with the extraction reactor.

Statement 20. A system according to Statement 15-19, where the system operates continuously or in a semi-batch mode.

The following examples are presented to illustrate the present disclosure. They are not intended to be limiting in any matter.

Example 1

This example describes preparation and characterization of fluoroponytailed 14-crown-4 ethers.

A novel type of crown ethers, fluoroponytailed 14-crown-4 ethers, were synthesized. These crown ethers have desirable lithium selectivity and are also highly soluble in supercritical carbon dioxide (or supercritical carbon dioxide with a co-solvent such as a simple alcohol or chlorinated solvent), thus enabling the operation of a continuous lithium extraction process into supercritical carbon dioxide when paired with a cation exchanger.

The novel 14-crown-4 ethers were synthesized by first synthesizing methylene-14-crown-4 according to published procedures and then attaching the fluorinated side chains through a UV light activated thiol-ene reaction (see FIG. 1 for an example of a synthetic pathway). The 14-crown-4 ethers can then be solubilized in either a co-solvent (simple alcohols or chlorinated solvents) or in the cation exchanger being used (e.g. HDEHP (di-(2-ethylhexyl)phosphoric acid), PFOA (perfluorooctanoic acid), HDDNS (didodecylnaphthalenesulfonic acid)) and pumped to pressure into a mixing cell where the mixture is heated and solubilized in supercritical carbon dioxide. The resulting mixture is then pumped into a cell with a lithium containing aqueous solution for lithium extraction. This process can be operated in a continuous manner to facilitate a continuous extraction process.

Example 2

This example describes the use of the fluoroponytailed 14-crown-4 ethers of the present disclosure for the extraction of lithium metal ions.

This example describes efficient and selective extraction of lithium into supercritical carbon dioxide (with or without a co-solvent such as a simple alcohol or chlorinated solvent) using a synergistic extraction system with a fluoroponytailed 14-crown-4 ether extractant and a cation exchanger.

By coupling novel and supercritical carbon dioxide soluble 14-crown-4 ethers with lipophilic cation exchangers, an environmentally friendly extraction system that is selective to lithium and can be operated in a continuous fashion was developed. Both the novel 14-crown-4 ether and the lipophilic cation exchanger are necessary for the successful extraction of lithium into the supercritical carbon dioxide phase.

The extractants are fluoroponytailed 14-crown-4 ethers, the fluoroponytail being added to enhance solubility in supercritical carbon dioxide, and they are paired with lipophilic cation exchangers that are soluble in supercritical carbon dioxide at the operating conditions, such as HDEHP (di-(2-ethylhexyl)phosphoric acid), PFOA (perfluorooctanoic acid), and HDDNS (didodecylnaphthalenesulfonic acid).

The two figures below (FIGS. 2 and 3) show examples of a small-scale set up for the operation of the process described here and how the process is expected to be operated on an industrial scale, respectively. The fluoroponytailed 14-crown-4 ether extractant can either be dissolved in the cation exchanger before pumping it into the system or it can be dissolved along with the cation exchanger in a co-solvent such as a simple alcohol (methanol, ethanol, etc.) or a chlorinated solvent. This mixture is pumped into a stream of carbon dioxide and mixed with the carbon dioxide at supercritical conditions in a mixing cell. The mixture is then pumped to an extraction reactor where it comes into contact with a flow of an aqueous solution containing dissolved lithium salt. Lithium is extracted from the aqueous solution in the extraction reactor, into the supercritical carbon dioxide phase. The supercritical carbon dioxide phase then goes through a pressure drop to condense the lithium containing complex out into an organic solvent.

A description of an example process:
1) Provide a source of carbon dioxide;
2) Pump the carbon dioxide to a pressure at or above its critical point in a mixing cell, heated to a temperature at or above its critical point;
3) Provide a source of one or more fluoroponytailed 14-crown-4 ether and one or more supercritical carbon dioxide soluble cation exchanger mixed together (or dissolved in a co-solvent);
4) Pump the fluoroponytailed 14-crown-4 ether and cation exchanger into the mixing cell to a pressure where the fluoroponytailed 14-crown-4 ether, cation exchanger (and, optionally, one or more co-solvent) and the carbon dioxide form a single phase upon mixing;
5) Pump the mixture at a constant pressure and temperature to an extraction reactor where it comes into contact with a lithium salt containing aqueous solution. The mixture is pumped through the lithium salt containing aqueous solution, in a continuous or semi-batch mode (lithium containing solution being the stationary phase in semi-batch operation mode);
6) Lithium is extracted into the carbon dioxide mixture in the extraction reactor through a reaction with the fluoroponytailed 14-crown-4 ether and the cation exchanger. It forms a lithium containing complex that is dissolved in the carbon dioxide mixture;
7) The lithium complex impregnated carbon dioxide mixture is pumped from the extraction reactor through a pressure reducing valve. The pressure is reduced such that the lithium containing complex comes out of solution and is captured in an organic solvent. The organic solvent then goes through a back-extraction process where it comes in contact with a mineral acid (e.g. hydrochloric acid, sulfuric acid, phosphoric acid, nitric acid) in an extraction reactor. In the back-extraction the lithium containing complex breaks apart, the lithium is transferred to the mineral acid and the regenerated extractant and regenerated cation exchanger remain in the organic solvent.
8) A process wherein the regenerated extractant and cation exchanger dissolved in the organic solvent are used as the source that is pumped into the mixing cell. A method can comprise all or a combination of these steps.

An alternate version of this method is the operation of a similar system in semi-batch mode. In that case, the supercritical carbon dioxide that is impregnated with a fluoroponytailed 14-crown-4 ether extractant and a cation exchanger is pumped through a stationary aqueous phase in a tank. A process operated in this way still requires that the 14-crown-4 ether extractant be highly soluble in supercritical carbon dioxide. It retains the efficiency of the continuous process and maintains its environmentally friendly features.

Although the present disclosure has been described with respect to one or more particular embodiments and/or examples, it will be understood that other embodiments and/or examples of the present disclosure may be made without departing from the scope of the present disclosure.

What is claimed is:
1. A method for removing lithium ions from an aqueous solution comprising lithium ions comprising:
contacting the aqueous solution comprising lithium ions with one or more fluorinated crown ether(s) having the following structure:

wherein R is an exocyclic fluorinated group and s is 1, 2, 3, 4, 5, 6, 7, 8, 9, or 10 and the exocyclic fluorinated group comprises a terminal fluorinated group, wherein the terminal fluorinated group is independently at each occurrence or wherein n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F, and
contacting the aqueous solution with a cation exchanger, and
separating the aqueous solution that has been contacted with the one or more fluorinated crown ether(s) and the cation exchanger resulting in removal of at least a portion of or all of the lithium ions from the aqueous solution.

2. The method of claim 1, further comprising removing lithium ions from the one or more fluorinated crown ether(s) and the cation exchanger that has been contacted with the aqueous solution by washing the one or more fluorinated crown ether(s) and the cation exchanger that has been contacted with the sample with a mineral acid.

3. The method of claim 2, wherein the one or more fluorinated crown ether(s) is/are recycled.

4. The method of claim 1, wherein the cation exchanger is contacted with the aqueous solution after the aqueous solution is contacted with the one or more fluorinated crown ether(s).

5. The method of claim 1, wherein the contacting is carried out in a batch mode, semi-batch mode or a continuous mode.

6. The method of claim 1, wherein the aqueous solution is selected from the group consisting of lithium brine, geothermal water, oilfield brine, fluid produced in a fracking operation, wastewater, desalination plant runoff, battery recycling fluid, and seawater.

7. The method of claim 1, wherein the contacting is carried out with a mixture comprising the aqueous solution, the one or more fluorinated crown ether(s), the cation exchanger, and carbon dioxide.

8. The method of claim 1, wherein the fluorinated crown ether(s) has/have the following structure:

9. The method of claim 1, wherein the fluorinated crown ether(s) has/have the following structure:

or

10. The method of claim 1, wherein the aqueous solution is an aqueous sample.

11. A system for performing the method of claim 1, for removing lithium ions from an aqueous solution comprising lithium ions comprising:

a fluorinated crown ether extractant and cation exchanger-containing source comprising one or more fluorinated crown ether(s), each fluorinated crown ether independently having the following structure:

wherein R is an exocyclic fluorinated group and s is 1, 2, 3, 4, 5, 6, 7, 8, 9, or 10 and the exocyclic fluorinated group comprises a terminal fluorinated group, wherein the terminal fluorinated group is independently at each occurrence wherein n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F, and a cation exchanger for contacting the aqueous solution;

a carbon dioxide source;

a mixing cell in fluid communication with the fluorinated crown ether extractant and cation exchanger source and the carbon dioxide source;

an aqueous solution source configured to provide a lithium ion containing aqueous solution;

an extraction reactor in fluid communication with the mixing cell and the aqueous solution source, wherein lithium ions are extracted, separated, and removed from the lithium ion containing aqueous solution in the extraction reactor into the supercritical carbon dioxide phase;

a pressure reducing valve in fluid communication with the extraction reactor; and a collection vessel in fluid communication with the pressure reducing valve, wherein the collection vessel collects a condensed lithium containing complex.

12. The system of claim 11, wherein the mixing cell operates at supercritical conditions.

13. The system of claim 11, wherein the system operates continuously or in a semi-batch mode.

14. A system for performing the method of claim 1, for removing lithium ions from an aqueous solution comprising lithium ions comprising:

an aqueous solution source configured to provide the aqueous solution;

a fluorinated crown ether extractant and cation exchanger-containing source, and a carbon dioxide source, respectively, comprising one or more fluorinated crown ether extractant(s) and a cation exchanger for contacting the aqueous sample, and carbon dioxide, wherein each fluorinated crown ether extractant independently has the following structure:

wherein R is an exocyclic fluorinated group and s is 1, 2, 3, 4, 5, 6, 7, 8, 9, or 10 and the exocyclic fluorinated group comprises a terminal fluorinated group, wherein
the terminal fluorinated group is independently at each occurrence wherein n is, independently at each occurrence, 2, 3, 4, 5, 6, 7, 8, 9, 10, 11, 12, 13, 14, 15, 16, 17, 18, 19, or 20; m is, independently at each occurrence, 0, 1, 2, 3, 4, 5, 6, 7, 8, 9, 10, 11, 12, 13, 14, 15, 16, 17, 18, 19, or 20; a, b, c, d, are, independently at each occurrence, 0, 1, 2, 3, 4, 5, 6, 7, 8, 9, 10, 11, 12, 13, 14, 15, 16, 17, 18, 19, or 20; and A is, independently at each occurrence, H or F;

an extraction reactor in fluid communication with the aqueous solution source and the fluorinated crown ether extractant, cation exchanger, and carbon dioxide source;

a condenser in fluid communication with the extraction reactor, wherein the condenser condenses at least some of a lithium containing complex from a carbon dioxide stream that includes the lithium containing complex into an organic solvent;

a compressor in fluid communication with the condenser, wherein the compressor compresses at least some of the carbon dioxide stream that is depleted of the lithium containing complex;

a second extraction reactor in fluid communication with the condenser, wherein the organic solvent comprising the lithium containing complex is delivered to the second extraction reactor, the extraction reactor and the second extraction reactor operable for separating and removing the lithium ions from the aqueous solution;

a mineral acid source in fluid communication with the second extraction reactor;

a first collection vessel in fluid communication with the second extraction reactor, wherein the first collection vessel collects lithium impregnated mineral acid; and a second collection vessel in fluid communication with the second extraction reactor, wherein the second collection vessel collects lithium depleted organic solvent.

15. The system of claim 14, wherein the fluorinated crown ether extractant(s) and the cation exchanger from the fluorinated crown ether extractant source and the cation exchanger source and the carbon dioxide from the carbon dioxide source are both delivered to the extraction reactor through a conduit.

16. The system of claim 14, wherein carbon dioxide from the carbon dioxide source is at a pressure at or above its critical point and/or is at a temperature at or above its critical point.

17. The system of claim 14, wherein the compressor is in fluid communication with the extraction reactor.

18. The system of claim 14, wherein the system operates continuously or in a semi-batch mode.

* * * * *